US011966270B2

United States Patent
Isogai et al.

(10) Patent No.: US 11,966,270 B2
(45) Date of Patent: Apr. 23, 2024

(54) SENSOR DATA COLLECTION DEVICE, SENSOR DATA COLLECTION SYSTEM, AND METHOD OF COLLECTING SENSOR DATA

(71) Applicant: Seiko Group Corporation, Tokyo (JP)

(72) Inventors: Ryosuke Isogai, Chiba (JP); Yoshifumi Yoshida, Chiba (JP)

(73) Assignee: SEIKO GROUP CORPORATION, Tokyo (JP)

( * ) Notice: Subject to any disclaimer, the term of this patent is extended or adjusted under 35 U.S.C. 154(b) by 5 days.

(21) Appl. No.: 17/872,332

(22) Filed: Jul. 25, 2022

(65) Prior Publication Data
US 2023/0024793 A1 Jan. 26, 2023

(30) Foreign Application Priority Data
Jul. 26, 2021 (JP) ................................ 2021-121874

(51) Int. Cl.
*G06F 1/32* (2019.01)
*G06F 1/3225* (2019.01)
*G06F 1/3287* (2019.01)

(52) U.S. Cl.
CPC .......... *G06F 1/3225* (2013.01); *G06F 1/3287* (2013.01)

(58) Field of Classification Search
None
See application file for complete search history.

(56) References Cited

U.S. PATENT DOCUMENTS

| | | | | |
|---|---|---|---|---|
| 11,307,632 B2* | 4/2022 | Karthikeyan | ......... | G06F 1/3287 |
| 2012/0096288 A1* | 4/2012 | Bates | ...................... | G06F 1/206 |
| | | | | 713/320 |
| 2014/0129866 A1* | 5/2014 | Hallman | ................. | H04L 67/12 |
| | | | | 713/340 |
| 2016/0029315 A1* | 1/2016 | Kates | ................... | G08B 25/001 |
| | | | | 340/602 |
| 2016/0132099 A1* | 5/2016 | Grabau | ................. | G06F 1/3215 |
| | | | | 713/323 |

(Continued)

FOREIGN PATENT DOCUMENTS

JP 2280001102 3/2014

*Primary Examiner* — Jaweed A Abbaszadeh
*Assistant Examiner* — Cheri L Harrington
(74) *Attorney, Agent, or Firm* — Crowell & Moring LLP

(57) ABSTRACT

There are provided a sensor data collection device, a sensor data collection system, and a method of collecting sensor data capable of reducing a drain of a battery due to standby power. The sensor data collection device includes a power supply, a power supply control circuit configured to control the power supply, a sensor configured to perform sensing to thereby obtain data, a memory configured to store the data obtained by the sensor, and a control circuit configured to control the power supply control circuit, the sensor, and the memory. The power supply control circuit supplies the sensor, the memory, and the control circuit with electrical power supplied by the power supply, and the control circuit makes the transition to any one of a plurality of operating states, and makes the power supply control circuit shut off the electrical power supplied by the power supply after a first operating state is completed and before the transition to a second operating state is made wherein the first operating state and the second operating state are included in the plurality of operating states.

13 Claims, 8 Drawing Sheets

(56) References Cited

U.S. PATENT DOCUMENTS

| | | |
|---|---|---|
| 2019/0341803 A1* | 11/2019 | Cook ..................... H02J 9/061 |
| 2019/0369711 A1* | 12/2019 | Wang .................... G06F 1/3212 |
| 2020/0037272 A1 | 1/2020 | Fujimori et al. |
| 2020/0137215 A1* | 4/2020 | Zhou ..................... G01S 7/4876 |
| 2020/0158556 A1* | 5/2020 | Strutt .................. G01S 7/52004 |
| 2022/0346022 A1* | 10/2022 | Butt .................. H04W 52/0251 |

\* cited by examiner

SENSOR DATA COLLECTION DEVICE, SENSOR DATA COLLECTION SYSTEM, AND METHOD OF COLLECTING SENSOR DATA

RELATED APPLICATIONS

This application claims priority to Japanese Patent Application No. 2021-121874, filed on Jul. 26, 2021, the entire content of which is incorporated herein by reference.

BACKGROUND OF THE INVENTION

1. Field of the Invention

The present disclosure relates to a sensor data collection device, a sensor data collection system, and a method of collecting sensor data.

2. Description of the Related Art

There is known a sensor system provided with a sensor terminal for collecting data, and a data collection device to be coupled to the sensor terminal via wireless communication.

In the sensor system, the sensor terminal encrypts sensor data obtained by measurement performed by the sensor device in accordance with a measurement parameter received using an encryption key received, and then transmits the sensor data thus encrypted to the data collection device.

The data collection device decrypts the sensor data received from the sensor terminal, and when the sensor data is normally decrypted, the data collection device stores the sensor data thus decrypted in a storage section, and when the sensor data fails to normally be decrypted, the data collection device discards the sensor data not having been decrypted, and transmits the measurement parameter and the encryption key to the sensor terminal.

Regarding the data collection device, there is known a technology in which a microcomputer gets into a sleep state in a non-operating state to achieve reduction in electrical power (see, e.g., JP-A-2020-021990).

Further, regarding a biological information measurement device, there is known a technology in which a microcomputer gets into a sleep state when the measurement is completed a predetermined number of times to reduce the power consumption (see, e.g., JP-A-2015-188558).

In general, the microcomputer has a standby (sleep) function, and reduces the power consumption using the standby function during the period in which a CPU (Central Processing Unit) does not operate. However, when using a small battery low in battery capacity is used as a power supply, and a long battery life is required, the power consumption by the standby power matters in some cases.

Further, even when the power consumption is suppressed due to the standby function of the microcomputer, power consumption due to other components coupled to the power supply than the microcomputer exists in some cases. As the power consumption due to other components coupled to the power supply than the microcomputer, there can be cited, for example, a leakage current of a capacitor, and power consumption due to other ICs than the microcomputer.

There is a device which makes the sensor operate a certain number of times to collect data, makes the transition to the standby state for a long period of time after accumulating the data thus collected, and then transmits the accumulated data to the outside after making the transition from the standby state to a start-up state. An example of this device is a sensor device, and the sensor device is installed in a place where the power supply and the communication environment do not exist, performs a required measurement to thereby collect data, and is then retrieved after completing accumulation of the data thus collected. It takes a period of several months for the sensor device in some cases until the sensor device is retrieved from when the collected data is accumulated.

Such a device is kept in the standby state until a data transmission instruction is received. Therefore, when it takes a long period for such a device until the data transmission instruction is received, there is a possibility that the battery drains more than expected only by the standby power. When the buttery drains more than the power necessary for the operation of transmitting the data to the outside, it becomes unachievable for such a device to retrieve the data.

The present disclosure is made in view of the problems described above, and has an object of providing a sensor data collection device, a sensor data collection system, and a method of collecting sensor data capable of reducing a drain of a battery due to the standby power.

SUMMARY OF THE INVENTION (1) In view of the problems described above, the sensor data collection device according to an aspect of the present disclosure includes a power supply, a power supply control circuit configured to control the power supply, a sensor configured to perform sensing to thereby obtain data, a memory configured to store the data obtained by the sensor, and a control circuit configured to control the power supply control circuit, the sensor, and the memory, wherein the power supply control circuit supplies the sensor, the memory, and the control circuit with electrical power supplied by the power supply, and the control circuit makes a transition to any one of a plurality of operating states, and makes the power supply control circuit shut off the electrical power supplied by the power supply after a first operating state is completed and before a transition to a second operating state is made, the first operating state and the second operating state being included in the plurality of operating states.

(2) In the sensor data collection device according to the aspect of the present disclosure, the power supply can be a primary cell or a secondary cell.

(3) In the sensor data collection device according to the aspect of the present disclosure, the power supply control circuit can include a switch and a switch control circuit, and the switch control circuit can open the switch to thereby shut off the electrical power to be supplied by the power supply.

(4) In the sensor data collection device according to the aspect of the present disclosure, the power supply control circuit can start the first operating state or the second operating state based on an external signal.

(5) In the sensor data collection device according to the aspect of the present disclosure, the switch control circuit can include a power generation element, and the switch control circuit can generate the external signal with electrical power generated by the power generation element.

(6) In the sensor data collection device according to the aspect of the present disclosure, the power generation element can be a photovoltaic generation element, and the switch control circuit can generate the external signal with the photovoltaic power caused by light irradiation to the photovoltaic generation element.

(7) In the sensor data collection device according to the aspect of the present disclosure, the control circuit can make the sensor periodically obtain data, and then make the memory store the data obtained in the first operating state, and can make a wireless communication section transmit data accumulated in the memory to an outside in the second operating state.

(8) In the sensor data collection device according to the aspect of the present disclosure, the control circuit can make the power supply control circuit shut off the electrical power to be supplied by the power supply when an exceptional matter occurs during an operation.

(9) In the sensor data collection device according to the aspect of the present disclosure, the control circuit can further include a determination section configured to determine whether or not there remains a battery level for transmitting data accumulated in the memory in the second operating state, and a creation section configured to create a summary of the data accumulated in the memory when the determination section determines that the battery level for transmitting the data does not remain, and the control circuit can make a wireless communication section transmit the summary of the data created by the creation section in the second operating state.

(10) In the sensor data collection device according to the aspect of the present disclosure, the control circuit can transmit a power-off signal to the power supply control circuit when the control circuit makes the power supply control circuit shut off the electrical power to be supplied by the power supply, and the power-off signal can be transmitted to the power supply control circuit via a signal holding circuit.

(11) In the sensor data collection device according to the aspect of the present disclosure, the signal holding circuit can be configured including a capacitor and can be arranged to hold a charge.

(12) A sensor data collection system according to an aspect of the present disclosure includes the sensor data collection device according to any one of (1) through (11), and an external device which is configured to generate an external signal for making the sensor data collection device start the second operating state after the sensor data collection device makes the power supply control circuit shut off the power to be supplied by the power supply.

(13) A method of collecting sensor data according to an aspect of the present disclosure is a method of collecting sensor data to be executed by a sensor data collection device including a power supply, a power supply control circuit configured to control the power supply, a sensor configured to perform sensing to thereby obtain data, a memory configured to store the data obtained by the sensor, and a control circuit configured to control the power supply control circuit, the sensor, and the memory, the method including the steps of supplying, by the power supply control circuit, the sensor, the memory, and the control circuit with electrical power supplied by the power supply, and making, by the control circuit, the power supply control circuit shut off the electrical power supplied by the power supply after a first operating state is completed, and before a transition to a second operating state is made.

According to the present disclosure, it is possible to provide a sensor data collection device, a sensor data collection system, and a method of collecting sensor data capable of reducing a drain of a battery due to standby power.

DETAILED DESCRIPTION OF THE PREFERRED EMBODIMENTS

Then, a sensor data collection device, a sensor data collection system, and a method of collecting sensor data according to the present embodiment will be described with reference to the drawings. The embodiment described hereinafter is illustrative only, and embodiments to which the present disclosure is applied are not limited to the embodiment described below.

Further, "based on XX" described in the present application means "based at least on XX," and includes the case in which something is based on other elements in addition to XX. Further, "based on XX" is not limited to the case in which XX is used directly, and includes the case in which something is based on what is obtained by performing a calculation or processing on XX. "XX" is an arbitrary element (e.g., arbitrary information).

Embodiment

An embodiment of the invention will hereinafter be described with reference to the drawings. Constituents having the same functions or similar functions are denoted by the same reference symbols, and redundant descriptions regarding the constituents will be omitted in some cases.

(Sensor Data Collection System)

Figure 1:
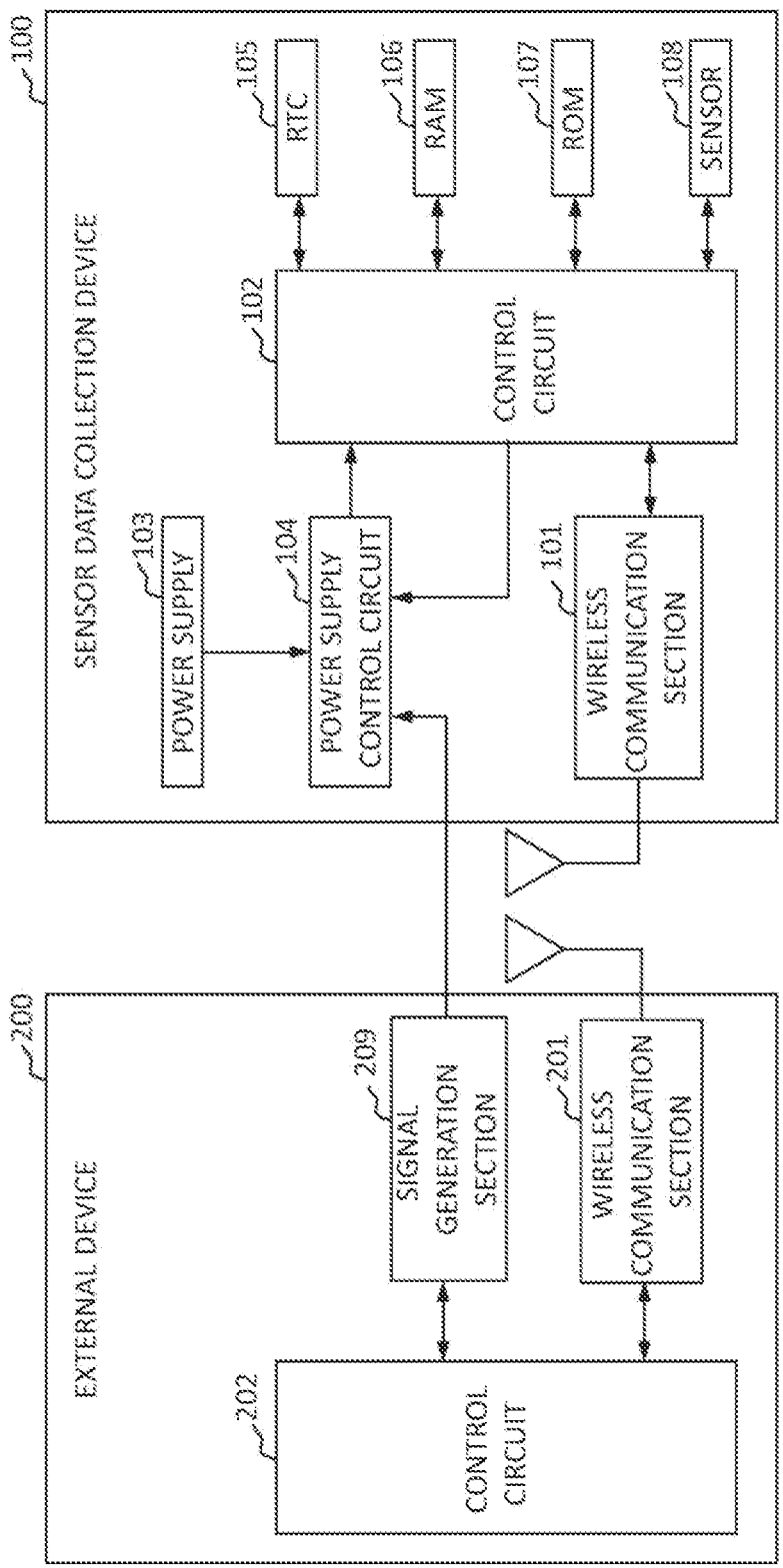
FIG. 1 is a diagram showing an example of a sensor data collection system according to an embodiment of the present disclosure.

FIG. 1 is a diagram showing an example of the sensor data collection system according to the embodiment of the present disclosure. A sensor data collection system 1 according to the present embodiment is provided with a sensor data collection device 100 and an external device 200.

(Sensor Data Collection Device 100)

The sensor data collection device 100 is provided with a wireless communication section 101, a control circuit 102, a power supply 103, a power supply control circuit 104, a real time clock (RTC) 105, a RAM (Random Access Memory) 106, a ROM (Read Only Memory) 107, and a sensor 108.

The sensor data collection device 100 can take one of a plurality of operating states. The plurality of operating states includes a first operating state, a power-off state, and a second operating state. When the sensor data collection device 100 is in the first operating state, the sensor data collection device 100 periodically makes the sensor 108 perform sensing to thereby obtain data, and makes the ROM 107 hold the data thus obtained.

The sensor data collection device 100 makes the power supply control circuit 104 shut off the power supplied by the power supply 103 to thereby make the transition to the power-off state after the first operating state is completed, and before the transition to the second operating state is made. The power-off state is a state in which the power supply 103 and a circuit coupled to the power supply control circuit 104 are electrically disconnected by a switch or the like included in the power supply control circuit. The switch mentioned here can be a load switch IC (Integrated Circuit), a MOSFET (Metal-Oxide-Semiconductor Field Effect Transistor), a JFET (Junction Field Effect Transistor), a transistor, or the like. The switch small in size and low in power consumption is preferable, and it is desirable to use, for example, a p-channel MOSFET.

The sensor data collection device 100 conducts the electrical power supplied by the power supply 103 to the power supply control circuit 104 based on an external signal to thereby make the transition to the second operating state. An example of the external signal is emitted by the external device 200, and is used as a trigger in the sensor data collection device 100. An example of the trigger is light, magnetism, a radio wave, an electric signal, or the like, and there is desired what does not consume the electrical power such as a solar cell or an energy harvesting technology in order to monitor the trigger in the sensor data collection device 100. The second operating state is a state in which the power supply 103 and a circuit coupled to the power supply control circuit 104 are electrically connected with the switch or the like included in the power supply control circuit. When the sensor data collection device 100 is in the second operating state, the sensor data collection device 100 transmits the data accumulated in the ROM 107 to the outside with wireless communication.

The wireless communication section 101 performs communication with the external device 200. An example of the wireless communication system used for the communication between the wireless communication section 101 and the external device 200 is Bluetooth Low Energy (BLE). It should be noted that it is possible to perform the wireless communication between the wireless communication section 101 and the external device 200 with a wireless communication system such as wireless LAN other than BLE.

Specifically, the wireless communication section 101 receives a start-up instruction signal transmitted by the external device 200. The start-up instruction signal is an example of the external signal. The wireless communication section 101 obtains the sensor data notification output by the control circuit 102, and then transmits the sensor data notification thus obtained to the external device 200.

The control circuit 102 controls the power supply control circuit 104, the RTC 105, the RAM 106, the ROM 107, and the sensor 108.

The power supply 103 supplies each section of the sensor data collection device 100 with the electrical power via the power supply control circuit 104. An example of the power supply 103 is a primary cell or a secondary cell. The sensor data collection device is not required to be provided with a device for charging the secondary cell.

The power supply control circuit 104 controls the power supply 103. The power supply control circuit 104 supplies the electrical power from the power supply 103 to each section of the sensor data collection device 100 such as the wireless communication section 101, the control circuit 102, the RTC 105, the RAM 106, the ROM 107, and the sensor 108.

Figure 2:
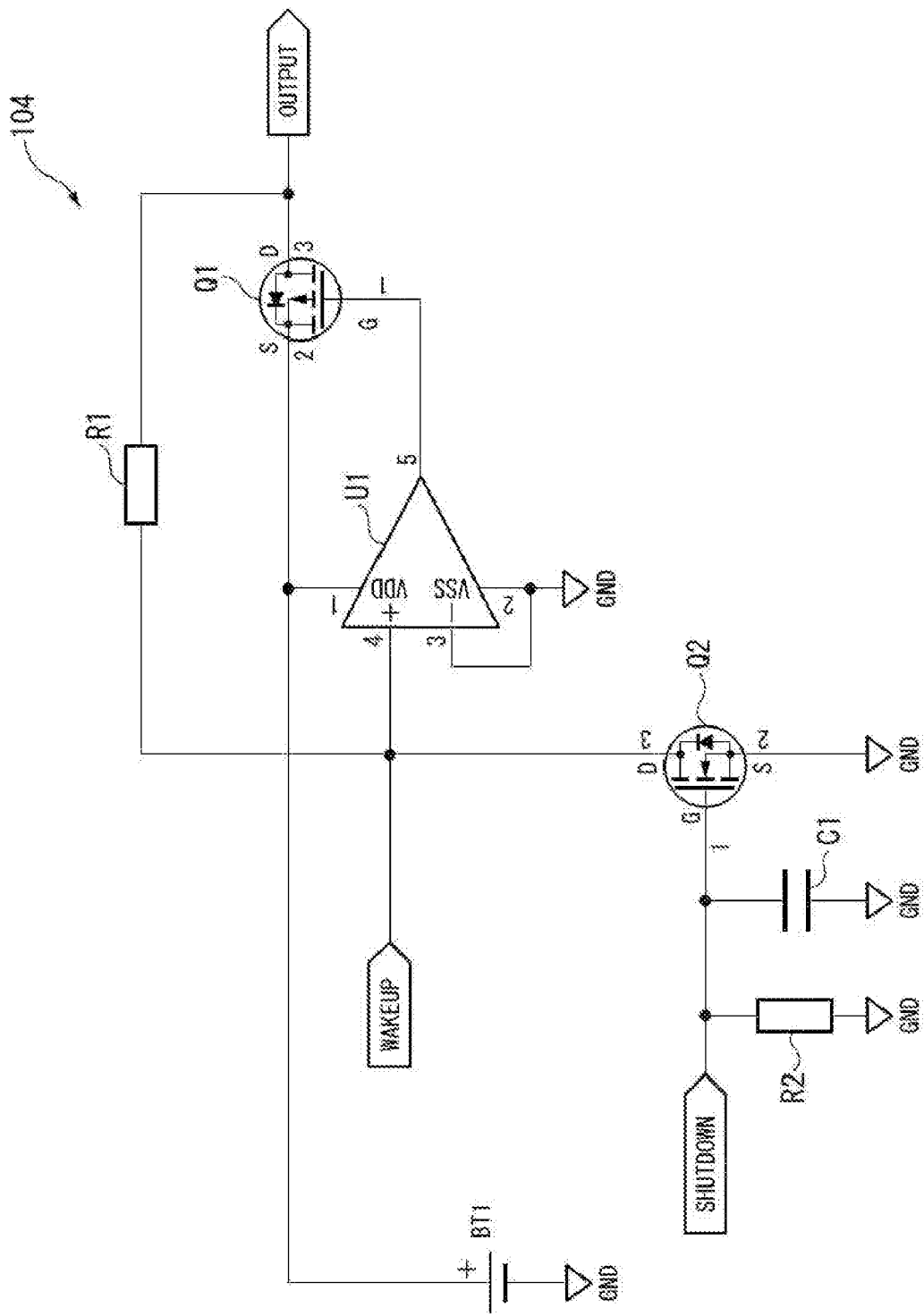
FIG. 2 is a diagram showing an example of a power supply control circuit provided to a sensor data collection device according to the embodiment.

FIG. 2 is a diagram showing an example of the power supply control circuit provided to the sensor data collection device according to the present embodiment. The power supply control circuit 104 includes a latch circuit and a shutoff circuit. The latch circuit is provided with an operational amplifier U1, a transistor Q1, and a resistor R1. The shutoff circuit is provided with a transistor Q2, a capacitor C1, and a resistor R2.

An example of an operation of the power supply control circuit 104 will be described. When a WAKEUP signal no lower than a specified voltage is input to the operational amplifier U1, the transistor Q1 is set to a conductive state, and thus, a battery voltage is output from OUTPUT. On this occasion, since OUTPUT is fed back to the operational amplifier by the resistor R1, the power supply is kept in the conductive state even when removing the WAKEUP signal.

When a signal no lower than a specified voltage is applied to SHUTDOWN in this state, the capacitor C1 is charged, and at the same time, the transistor Q2 is set to the conductive state to pull out the charge from the operational amplifier U1 (since a drain capacity of the transistor Q2 is higher than a feedback current via the resistor R1). On this occasion, when the SHUTDOWN signal is generated by a circuit powered by OUTPUT, the SHUTDOWN signal becomes in an invalid state in some cases. However, since an input of the transistor Q2 is kept at a high level by the capacitor C1, the transistor Q2 is kept in the conductive state until the charge is completely pulled out from the operational amplifier U1. It should be noted that the resistor R2 is a pull-down resistor for preventing the potential from floating when SHUTDOWN is in the invalid state.

The RTC 105 is a timepiece incorporated in a computer or the like, or an integrated circuit (IC) in which a timepiece function is implemented. It is possible for the RTC 105 to continue to tick "time" due to battery backup or the like even when the electrical power from the power supply 103 of the sensor data collection device 100 is shut off.

The RAM 106 is a short-term temporary storage area for making the sensor data collection device 100 operate.

The ROM 107 stores the data obtained by the sensor 108. An example of the ROM 107 is a nonvolatile memory.

The control circuit 102 obtains the start-up instruction signal received by the wireless communication section 101. The control circuit 102 starts control of the RTC 105, the RAM 106, the ROM 107, and the sensor 108 based on the start-up instruction signal thus obtained. For example, the control circuit 102 starts the measurement of the time by the RTC 105.

The control circuit 102 controls the sensor 108 to thereby make the sensor 108 periodically perform sensing. The sensor 108 performs the sensing to thereby obtain the data (sensing data). An example of the sensor 108 includes at least one of a temperature sensor, an acceleration sensor, a gyro sensor, a pressure sensor, a strain sensor, a pulse wave sensor, a pulse oximeter, a heartbeat sensor, and a laser sensor.

Here, the pulse wave sensor measures a pulse wave using light, the pulse oximeter measures a blood oxygen level using light, the heartbeat sensor measures a heartbeat using light, and the laser sensor measures a blood flow using a laser beam.

The control circuit 102 obtains the data which is obtained by the sensor 108 performing the sensing, and makes the RAM 106 temporarily hold the data thus obtained. The control circuit 102 makes the ROM 107 store the data which the RAM 106 is made to hold.

The control circuit 102 determines whether or not a predetermined condition is fulfilled. An example of the predetermined condition is an elapse of a predetermined period. A case where the predetermined condition is an elapse of a predetermined period (time) will hereinafter continuously be described as an example.

The control circuit 102 determines whether or not the predetermined period has elapsed based on the time measured by the RTC 105. When the control circuit 102 has determined that the predetermined period has elapsed, the control circuit 102 outputs a power-off signal for shutting off the connection to the power supply 103 to the power supply control circuit 104.

The power supply control circuit 104 obtains the power-off signal output by the control circuit 102. The power supply control circuit 104 switches the connection state to the power supply 103 from an electrically connected state to an electrically disconnected state using a switch or the like based on the power-off signal thus obtained. As a result, the sensor data collection device 100 makes the transition from the first operating state to the power-off state.

Specifically, the power supply control circuit 104 is provided with a switch (not shown) and a switch control circuit (not shown). The switch control circuit changes the switch from a connected state to an open state to thereby shut off the electrical power to be supplied by the power supply 103.

The power supply control circuit 104 switches the connection state to the power supply 103 to the electrically connected state based on the external signal. An example of the external signal is emitted by the external device 200, and is used as the trigger in the sensor data collection device 100. An example of the trigger is light, magnetism, a radio wave, an electric signal, or the like. A case where using the light as an example of the trigger will hereinafter continuously be described.

In this case, the switch control circuit is provided with a power generation element. The power generation element generates electrical power with photovoltaic power generated by, for example, a solar cell, a photodiode, a light emitting diode, or the like being irradiated with light. The switch control circuit generates the external signal with the electrical power generated by the power generation element. In the power supply control circuit 104, the switch control circuit electrically connects the power supply 103 and the power supply control circuit 104 to the switch based on the external signal.

By the power supply control circuit 104 switching the connection state to the power supply 103 to the electrically connected state, the electrical power is supplied to each section of the sensor data collection device 100 from the power supply 103 to thereby make the transition to the second operating state.

In the second operating state, the control circuit 102 obtains the data accumulated in the ROM 107 to create the sensor data notification which includes the data thus obtained, and the destination of which is the external device 200. The control circuit 102 outputs the sensor data notification thus created to the wireless communication section 101.

Figure 3:
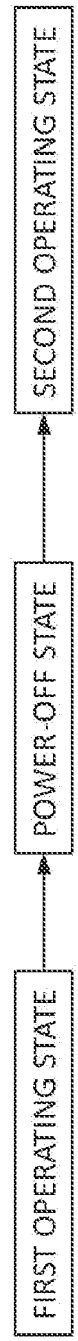
FIG. 3 is a diagram showing an example of operating states of the sensor data collection device according to the embodiment.

FIG. 3 is a diagram showing an example of operating states of the sensor data collection device according to the embodiment. The example of the operating states of the sensor data collection device 100 has the first operating state, the power-off state, and the second operating state.

The sensor data collection device 100 makes the transition from the first operating state to the power-off state, and makes the transition from the power-off state to the second operating state. In other words, the sensor data collection device 100 basically makes the one-way transition from the first operating state to the second operating state via the power-off state.

The sensor data collection device 100 accumulates the data obtained by the sensor 108 performing sensing in the first operating state. The sensor data collection device 100 makes the power supply control circuit 104 electrically disconnect the connection state to the power supply 103 in the first operating state based on the power-off signal output by the control circuit 102 to thereby make the transition to the power-off state.

The sensor data collection device 100 makes the power supply control circuit 104 electrically connect the connection state to the power supply 103 in the power-off state based on the external signal to thereby make the transition to the second operating state.

The sensor data collection device 100 obtains the data accumulated in the ROM 107 in the second operating state. The sensor data collection device 100 creates the sensor data notification which includes the data thus obtained, and the destination of which is the external device 200. The sensor data collection device 100 transmits the sensor data notification thus created to the external device 200. Going back to FIG. 1, the explanation is continued therefrom.

(External Device 200)

The external device 200 is provided with a wireless communication section 201, a control circuit 202, and a signal generation section 209.

The wireless communication section 201 performs communication with the sensor data collection device 100. An example of the wireless communication system used for the communication between the wireless communication section 201 and the sensor data collection device 100 is Bluetooth Low Energy. It should be noted that it is possible to perform the wireless communication between the wireless communication section 201 and the sensor data collection device 100 with the wireless communication system such as wireless LAN other than BLE.

Specifically, the wireless communication section 201 obtains the start-up instruction signal output by the control circuit 202. The wireless communication section 201 transmits the start-up instruction signal thus obtained to the sensor data collection device 100. The wireless communication section 201 receives the sensor data notification transmitted by the sensor data collection device 100.

The control circuit 202 controls the wireless communication section 201 and the signal generation section 209. The control circuit 202 creates the start-up instruction signal, and then outputs the start-up instruction signal thus created to the wireless communication section 201. The control circuit 202 creates an external signal generation request for generating the external signal, and then outputs the external signal generation request thus created to the signal generation section 209. The control circuit 202 obtains the sensor data notification received by the wireless communication section 201. The control circuit 202 performs predetermined processing on the sensor data notification thus obtained.

The signal generation section 209 generates the external signal based on the external signal generation request output by the control circuit 202.

(Operation of Sensor Data Collection System)

An operation of the sensor data collection system will be described.

Figure 4:
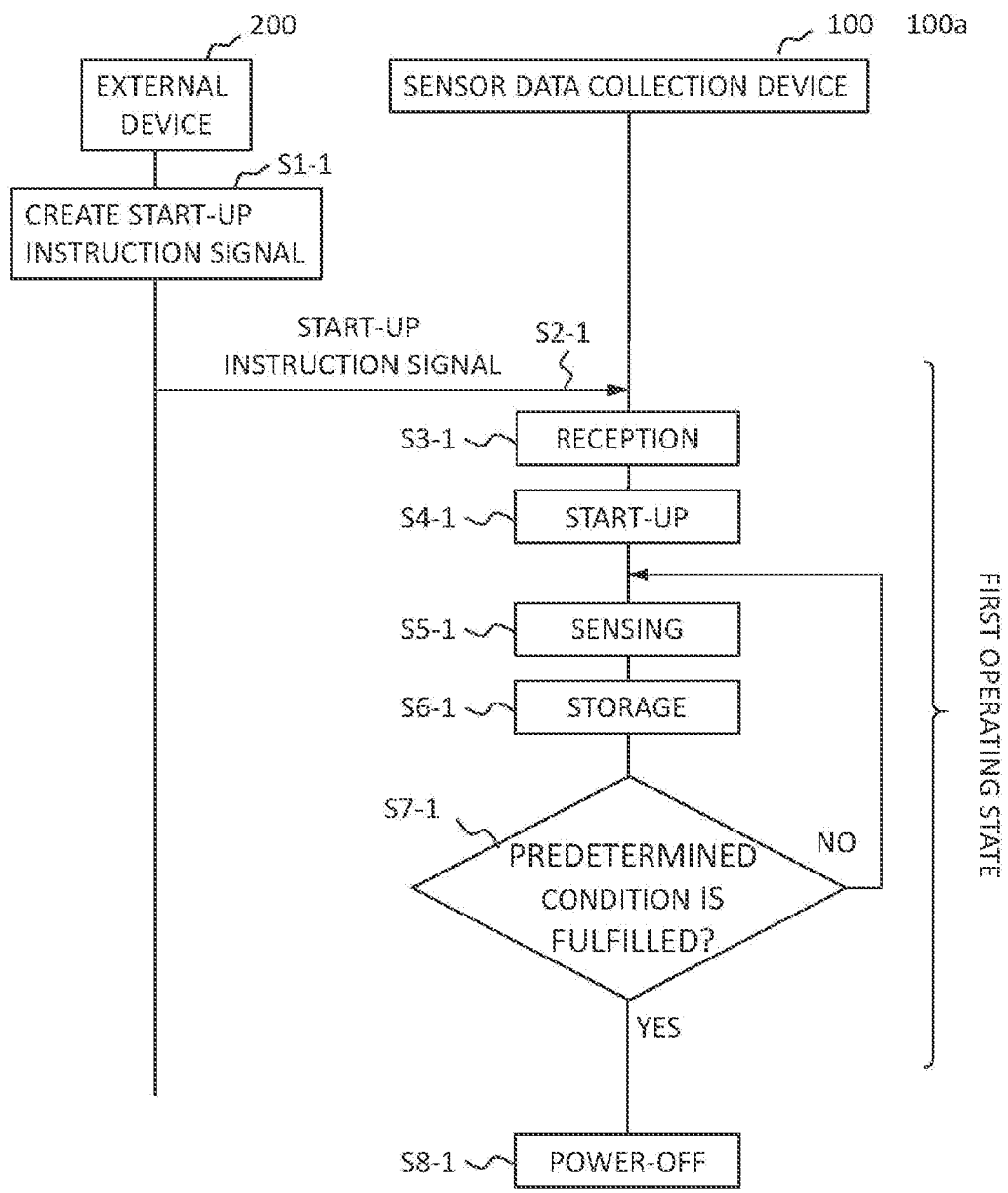
FIG. 4 is a flowchart showing Example 1 of an operation of the sensor data collection system according to the embodiment.

FIG. 4 is a flowchart showing Example 1 of the operation of the sensor data collection system according to the present embodiment. The operation in a case where the sensor data collection device 100 is in the first operating state in the sensor data collection system will be described with reference to FIG. 4.

(Step S1-1)

In the external device 200, the control circuit 202 creates the start-up instruction signal.

(Step S2-1)

In the external device 200, the control circuit 202 outputs the start-up instruction signal thud created to the wireless communication section 201. The wireless communication section 201 obtains the start-up instruction signal output by the control circuit 202. The wireless communication section 201 transmits the start-up instruction signal thus obtained to the sensor data collection device 100.

(Step S3-1)

In the sensor data collection device 100, the wireless communication section 101 receives the start-up instruction signal transmitted by the external device 200.

(Step S4-1)

In the sensor data collection device 100, the control circuit 102 obtains the start-up instruction signal received by the wireless communication section 101. The control circuit 102 starts the control of the RTC 105, the RAM 106, the ROM 107, and the sensor 108 based on the start-up instruction signal thus obtained. The control circuit 102 starts the measurement of the time by the RTC 105.

(Step S5-1)

In the sensor data collection device 100, the control circuit 102 controls the sensor 108 to thereby make the sensor 108 perform sensing. The sensor 108 performs the sensing to thereby obtain the data (sensing data).

(Step S6-1)

In the sensor data collection device 100, the control circuit 102 obtains the data which is obtained by the sensor 108 performing the sensing, and makes the RAM 106 temporarily hold the data thus obtained. The control circuit 102 makes the ROM 107 store the data which the RAM 106 is made to hold.

(Step S7-1)

In the sensor data collection device 100, the control circuit 102 determines whether or not the predetermined condition is fulfilled. When the predetermined condition is not fulfilled, the transition to the step S5-1 is made.

(Step S8-1)

In the sensor data collection device 100, when the predetermined condition is fulfilled, the control circuit 102 outputs the power-off signal for shutting off the connection to the power supply 103 to the power supply control circuit 104. The power supply control circuit 104 obtains the power-off signal output by the control circuit 102. The power supply control circuit 104 switches the connection state to the power supply 103 to the electrically disconnected state using the switch or the like based on the power-off signal thus obtained.

In the flowchart shown in FIG. 4, the steps S3-1 through S7-1 correspond to the first operating state. By the power supply control circuit 104 switching the connection state to the power supply 103 to the electrically disconnected state, the transition from the first operating state to the power-off state is made.

Figure 5:
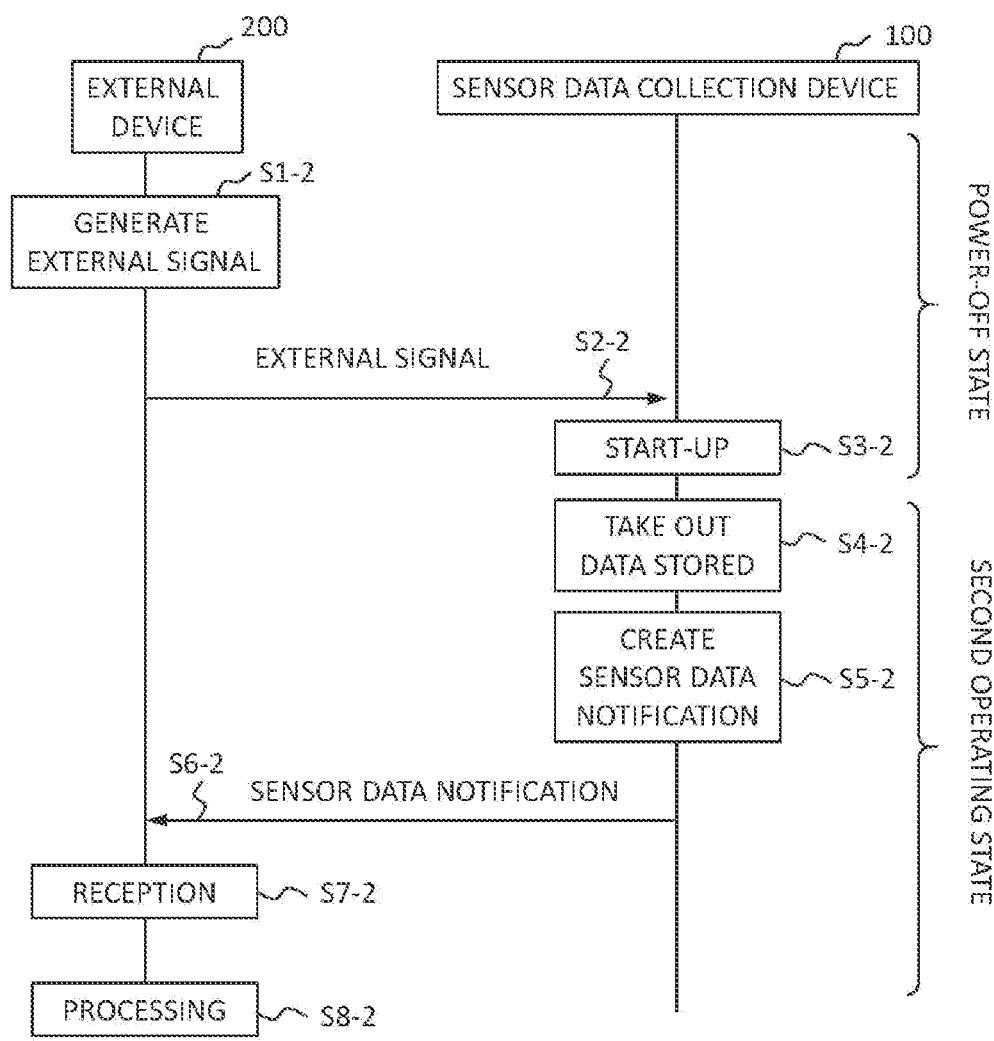
FIG. 5 is a flowchart showing Example 2 of an operation of the sensor data collection system according to the embodiment.

FIG. 5 is a flowchart showing Example 2 of the operation of the sensor data collection system according to the present embodiment. The operation when the sensor data collection device 100 is in the power-off state and the second operating state in the sensor data collection system will be described with reference to FIG. 5.

(Step S1-2)

In the external device 200, the control circuit 202 creates the external signal generation request for generating the external signal, and then outputs the external signal generation request thus created to the signal generation section 209.

(Step S2-2)

In the external device 200, the signal generation section 209 generates the external signal based on the external signal generation request output by the control circuit 202. The signal generation section 209 outputs the external signal thus generated to the sensor data collection device 100.

(Step S3-2)

In the sensor data collection device 100, the power supply control circuit 104 starts based on the external signal output by the external device 200. The power supply control circuit 104 switches the connection state to the power supply 103 from the electrically disconnected state to the electrically connected state using the switch or the like. By the power supply control circuit 104 switching the connection state to the power supply 103 from the disconnected state to the electrically connected state, the electrical power is supplied to each section of the sensor data collection device 100 from the power supply 103 to thereby start up the sensor data collection device 100.

(Step S4-2)

In the sensor data collection device 100, the control circuit 102 obtains the data accumulated in the ROM 107.

(Step S5-2)

In the sensor data collection device 100, the control circuit 102 creates the sensor data notification which includes the data thus obtained, and the destination of which is the external device 200.

(Step S6-2)

In the sensor data collection device 100, the control circuit 102 outputs the sensor data notification thus created to the wireless communication section 101. The wireless communication section 101 obtains the sensor data notification output by the control circuit 102, and then transmits the sensor data notification thus obtained to the external device 200.

(Step S7-2)

In the external device 200, the wireless communication section 201 receives the sensor data notification transmitted by the sensor data collection device 100.

(Step S8-2)

In the external device 200, the control circuit 202 obtains the sensor data notification received by the wireless communication section 201. The control circuit 202 performs the predetermined processing on the sensor data notification thus obtained.

In the flowchart shown in FIG. 5, the step S3-2 corresponds to the power-off state, and the steps S4-2 through S6-2 correspond to the second operating state.

In the embodiment described above, there is described a case where the sensor data collection device 100 accumulates the data obtained by the sensor 108 performing the sensing in the first operating state, but this example is not a limitation. For example, in the sensor data collection device 100, the control circuit 102 can be arranged to perform statistical processing such as counting the number of times the data obtained by the sensor 108 performing the sensing exceeds a predetermined threshold value, and then store the result of the statistical processing in the first operating state.

In the embodiment described above, there is described a case where the sensor data collection device 100 obtains the data accumulated in the ROM 107, creates the sensor data notification which includes the data thus obtained and the destination of which is the external device 200, and transmits the sensor data notification thus created to the external device 200 in the second operating state, but this example is not a limitation. For example, in the sensor data collection device 100, the control circuit 102 can be arranged to obtain the data accumulated in the ROM 107, perform arithmetic processing such as binarization, fast Fourier transform (FFT), or compression on the data thus obtained, then create the sensor data notification which includes the result of the arithmetic processing and the destination of which is the external device 200, and then transmit the sensor data notification thus created to the external device 200 in the second operating state.

In the embodiment described above, there is described a case where the control circuit 102 in the sensor data collection device 100 determines whether or not the predetermined period has elapsed, and then the control circuit 102 outputs the power-off signal for shutting off the connection to the power supply 103 to the power supply control circuit 104 when the control circuit 102 has determined that the predetermined period has elapsed, but this example is not a limitation.

For example, in the sensor data collection device 100, it is possible for the control circuit 102 to output the power-off signal for shutting off the connection to the power supply 103 to the power supply control circuit 104 to shut off the electrical power to be supplied by the power supply 103 when an exceptional matter occurs during the operation. An example of the exceptional matter is a case where an error occurs in the communication between the control circuit 102 and the sensor 108, and thus, it becomes difficult to accumulate the data in the ROM 107 in the first operating state, a case where the wireless connection is unintentionally shut off in the second operating state, or a case where the transition to the second operating state has unintentionally made due to some noise or disturbance.

It is assumed that the control circuit 102 gets into a runaway state, or is forcedly reset depending on the exceptional matter. In such a case, it is possible for the control circuit 102 to output the power-off signal for shutting off the connection to the power supply 103 to the power supply control circuit 104 to shut off the electrical power to be supplied by the power supply 103. Specifically, when the control circuit 102 is (forcedly) reset using a negative logic signal as the power-off signal, it is possible for the control circuit 102 to output the power-off signal to shut off the electrical power to be supplied by the power supply 103.

Further, it is possible for the control circuit 102 to be arranged to be provided with a monitor circuit for monitoring whether or not the control circuit 102 is operating normally. In this case, it is possible for the monitor circuit to be arranged to transmit the power-off signal to the power supply control circuit 104 when detecting the fact that the control circuit 102 is not normally operating.

By adopting such a configuration, it is possible to stably hold the data having ever been accumulated without idly draining the battery. Therefore, it is possible for the sensor data collection device 100 to surely perform the processing and the transmission of the data in the second operating state. Further, it is possible for the sensor data collection device 100 to be arranged to inform the user of the situation in which an error occurs when being retrieved.

In the embodiment described above, there is described a case where the sensor data collection device 100 conducts the electrical power supplied by the power supply 103 to the power supply control circuit 104 based on an external signal to thereby make the transition to the second operating state, but this example is not a limitation. For example, in the sensor data collection device 100, it is possible for the power supply control circuit 104 to be arranged to be provided with a timer inside. It is possible for the power supply control circuit 104 to be arranged to automatically be reconnected to the power supply 103 due to the expiry of the timer. By the power supply control circuit 104 being automatically reconnected to the power supply 103, the sensor data collection device 100 makes the transition to the second operating state.

By adopting such a configuration, it is possible to make the sensor data collection device 100 perform the operation for a sufficient period, then make the transition to the power-off state when accumulating a sufficient amount of data, and then make the transition to the second operating state at an appropriate timing set by the timer in advance. Therefore, it is possible for the user of the sensor data collection device 100 to collect the data at the appropriate timing for the convenience of the user.

In the embodiment described above, in order to ensure a pulse width of the power-off signal necessary for the power supply control circuit 104 to stably shut off the power supply 103, it is possible to arrange to provide a signal holding circuit between the control circuit 102 and the power supply control circuit 104. An example of the signal holding circuit is a latch circuit, a charge holding circuit, or the like.

When the power-off signal is transmitted by the control circuit 102 to the power supply control circuit 104, it is assumed that the power supply is shut off at the moment that the control circuit 102 transmits the power-off signal, and the power-off signal becomes in an invalid state. When the power-off signal becomes in the invalid state, the power supply is unintentionally reconnected due to a parasitic capacitance or an external noise in some cases.

Figure 6:
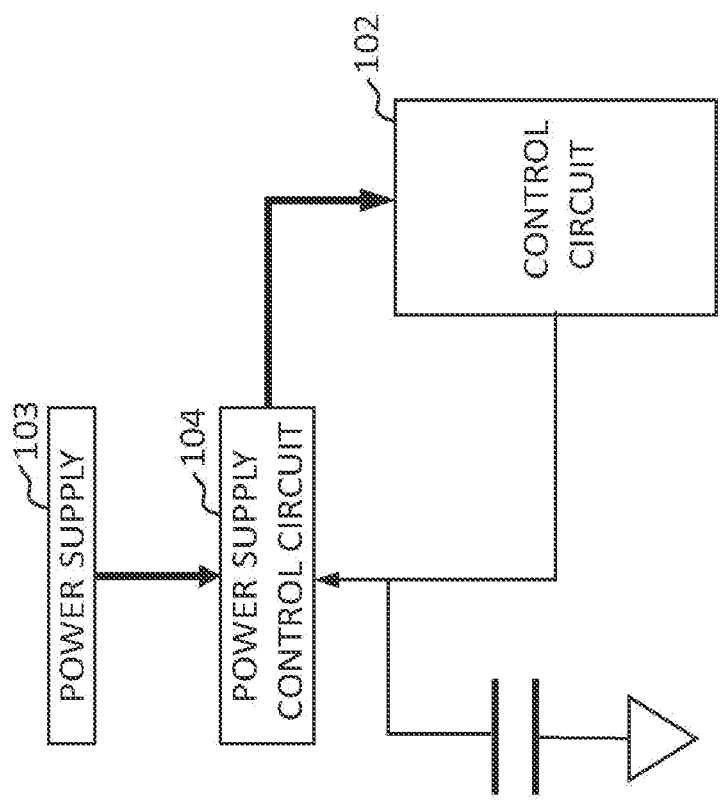
FIG. 6 is a diagram showing an example of a charge holding circuit provided to the sensor data collection device according to the embodiment.

FIG. 6 is a diagram showing an example of the charge holding circuit provided to the sensor data collection device according to the present embodiment. FIG. 6 shows the signal holding circuit using a capacitor as an example. An example of the signal holding circuit does not depend on the electrical power supplied from the power supply 103 to the power supply control circuit 104. According to this signal holding circuit, when an output impedance of a port of the power-off signal output by the control circuit 102 is sufficiently lower compared to an input impedance of the power supply control circuit, it is possible to keep the power-off signal in an active state for a sufficiently long period by the charge stored in the capacitor.

In the embodiment described above, a part or the whole of the processing of the control circuit 102 and the power supply control circuit 104 can also be a functional section (hereinafter referred to as a software functional section) realized by a processor such as a CPU (Central Processing Unit) executing a program stored in the ROM 107.

It should be noted that a part or the whole of the processing of the control circuit 102 and the power supply control circuit 104 can also be realized by hardware such as an LSI (Large Scale Integration), an ASIC (Application Specific Integrated Circuit), or an FPGA (Field-Programmable Gate Array), or can also be realized by a combination of the software functional section and the hardware.

According to the sensor data collection system 1 related to the present embodiment, the sensor data collection device 100 is provided with the power supply 103, the power supply control circuit 104 for controlling the power supply 103, the sensor 108 for obtaining the data by performing sensing, a memory as the ROM 107 for storing the data obtained by the sensor 108, and the control circuit 102 for controlling the power supply control circuit 104, and sensor 108, and the memory. The power supply control circuit 104 supplies the sensor 108, the memory, and the control circuit 102 with the electrical power supplied by the power supply 103. The control circuit 102 makes the transition to any one of the plurality of operating states, and makes the power supply control circuit 104 shut off the electrical power supplied by the power supply 103 after the first operating state is completed and before the transition to the second operating state is made wherein the first operating state and the second operating state are included in the plurality of operating states.

By adopting such a configuration, since it is possible for the control circuit 102 to make the power supply control circuit 104 shut off the electrical power supplied by the power supply 103 after the first operating state is completed and before the transition to the second operating state is made in the sensor data collection device 100, when a long standby period exists after the first operating state is completed and before the second operating state starts, it is possible to shut off the power supply 103 from the other circuits. The sensor data collection device 100 is capable of preventing the battery from draining due to the standby power, and is therefore capable of extending the life of the battery.

In a general device, there is adopted processing in which the control circuit gets into the standby state (the sleep state) so as to consume the electrical power as little as possible during the period between the first operating state and the second operating state. However, in the standby state, the electrical power is consumed although small in amount in order to keep the power supply for a block necessary to recover such as retention of the volatile memory or retention of a value of a register necessary for continuing the processing when recovering from the standby state. For example, when the power supply is a battery, and when using a battery extremely low in capacity, the small amount of power consumption matters in some cases.

Further, when the standby period between the first operating state and the second operating state is a long term no shorter than one month, or when a length of the period is left to the user, the problem of the small amount of power consumption becomes conspicuous.

An example of a usage in which the standby period between the first operating state and the second operating state is a long term no shorter than one month is a stationary wireless sensor device to be installed in a place without a communication environment and a power supply environment. The stationary wireless sensor device to be installed in a place without the communication environment and the power supply environment is retrieved by the user when a certain period has elapsed after the completion of the data accumulation. Assuming that the period from the completion of the data accumulation to the retrieval is in a range of several months through several years, there is a possibility that the remaining battery level completely drains due to the current consumed during the period.

It is assumed that the wireless sensor device is a device which is provided with a primary cell or a secondary cell, but is not provided with a charger, and which cannot be supplied with the electrical power from the outside. In this case, when the remaining battery level completely drains, it is unachievable to make the wireless sensor device operate after making the transition to the second operating state, and thus, it becomes unachievable to take out the data thus accumulated using a normal method.

In the sensor data collection device 100, the power supply 103 can be a primary cell or a secondary cell. In the case in which it is supposedly unachievable to charge the power supply 103, when the remaining battery level drains during the standby period between the first operating state and the second operating state, it becomes unachievable to start the second operating state.

By adopting such a configuration, the battery drain in the standby period can be made infinitely small. Therefore, in the usage with the long standby period, it is possible to omit the charging circuit from the sensor data collection device 100, and therefore it is possible to reduce the size of the sensor data collection device 100.

In the sensor data collection device 100, the power supply control circuit 104 is provided with the switch and the switch control circuit. The switch control circuit opens the switch to thereby shut off the electrical power to be supplied by the power supply 103.

By adopting such a configuration, the switch assumes the connection or disconnection between an input side (the power supply) and an output side (the circuits), and it is possible for the switch control circuit for controlling the switch to use the electrical power generated by the switch control circuit. Therefore, the power consumption when the power supply 103 is shut off from the power supply control circuit 104 can be made nearly zero. In other words, when the power supply 103 is shut off from the power supply control circuit 104, the switch control circuit is not supplied with the electrical power from the power supply 103.

In the sensor data collection device 100, the power supply control circuit 104 starts the first operating state or the second operating state based on the external signal.

It is possible for the power supply control circuit 104 to be provided with a device for starting the state transition such as a timer located inside, but there is consumed the electrical power for the timer to operate. By adopting such a configuration, it is possible to start the first operating state or the second operating state in accordance with the external signal transmitted from the outside of the sensor data collection device 100, and therefore, the power consumption in the standby state decreases, and it is possible to extend the life of the battery.

In the sensor data collection device 100, the switch control circuit is provided with the power generation element. The switch control circuit generates the external signal with the electrical power generated by the power generation element.

By adopting such a configuration, it is possible to switch the state of the switch between the disconnection and the connection using the electrical power obtained by the power generation with the power generation element, and therefore, it is possible to cover the necessary electrical power for flipping the switch with the power generation. Therefore, it becomes unnecessary to hold the necessary electrical power for flipping the switch when the power supply 103 is shut off from the power supply control circuit 104.

In the sensor data collection device 100, the power generation element is a photovoltaic generation element. The switch control circuit generates the external signal with the photovoltaic power caused by light irradiation to the photovoltaic generation element.

By adopting such a configuration, it is possible to use the photovoltaic generation element, and therefore, it is possible to perform the flip of the switch in a contactless manner. For example, it is possible to start the first operating state or the second operating state in a sealed device from the outside.

In the sensor data collection device 100, the control circuit 102 makes the sensor 108 periodically obtain the data, and then makes the memory store the data thus obtained in the first operating state, and makes the wireless communication section 101 transmit the data accumulated in the memory to the outside in the second operating state.

By adopting such a configuration, it is possible to define the first operating state as the operation of holding the data which is periodically obtained from the sensor 108 in the nonvolatile memory, and define the second operating state as the operation of transmitting the data accumulated in the nonvolatile memory to the outside. Therefore, when the control circuit 102 supposedly makes the sensor 108 perform the sensing operation until a specific condition such as the number of times is fulfilled, it is possible for the control circuit 102 to perform the extraction of the data without the charging or the replacement of the battery even when the standby period until the sensor data collection device 100 is retrieved is a long term of several months.

In the sensor data collection device 100, when an exceptional matter occurs during the operation, the control circuit 102 makes the power supply control circuit 104 shut off the electrical power to be supplied by the power supply 103.

By adopting such a configuration, when the exceptional matter such as an error, a failure of the sensor 108, a communication failure, or start-up caused by an unintentional external signal due to a noise occurs during the operation, the sensor data collection device 100 can immediately shut off the power supply 103 from the power supply control circuit 104, and can therefore avoid the runaway state and an idle standby of the microcomputer. Therefore, it is possible to prevent the drain of the battery to thereby newly start the second operating state once again.

In the sensor data collection device 100, when the control circuit 102 makes the power supply control circuit 104 shut off the electrical power to be supplied by the power supply 103, the control circuit 102 transmits the power-off signal to the power supply control circuit 104, and the power-off signal is transmitted to the power supply control circuit via the signal holding circuit.

When the power-off signal is transmitted from the control circuit 102 to the power supply control circuit 104, the power supply control circuit 104 and the power supply 103 are shut off from each other, but on this occasion, the transmission of the power-off signal is instantaneously interrupted to unintentionally reconnect the power supply control circuit 104 and the power supply 103 to each other in some cases.

By adopting such a configuration, it is possible to separately provide the signal holding circuit such as a latch circuit or a charge holding circuit independent of the power supply 103, and therefore, even after the power supply to the power supply control circuit 104 stops, it is possible to keep the power-off signal for a sufficient period of time to thereby surely cut the connection between the power supply (the battery) 103 and the power supply control circuit 104.

In the sensor data collection device 100, the signal holding circuit is configured including a capacitor and holds the charge.

By adopting such a configuration, the charge holding circuit formed of the capacitor can be used as the signal holding circuit, and therefore, it is possible to keep the power-off signal having a sufficient length for the power supply control circuit 104 to shut off the power supply 103 without an additional power supply.

According to the sensor data collection system 1 related to the present embodiment, the sensor data collection system 1 is provided with any one of the sensor data collection devices 100 described above, and the external device 200 which generates the external signal for making the sensor data collection device 100 start the second operating state after the sensor data collection device 100 makes the power supply control circuit 104 shut off the electrical power supplied by the power supply 103.

By adopting such a configuration, since it is possible for the control circuit 102 to make the power supply control circuit 104 shut off the electrical power supplied by the power supply 103 after the first operating state is completed and before the transition to the second operating state is made in the sensor data collection device 100, when a long standby period exists after the first operating state is completed and before the second operating state starts, it is possible to shut off the power supply 103 from the other circuits. The sensor data collection device 100 is capable of preventing the battery from draining due to the standby power, and is therefore capable of extending the life of the battery.

Modified Example of Embodiment

Figure 7:
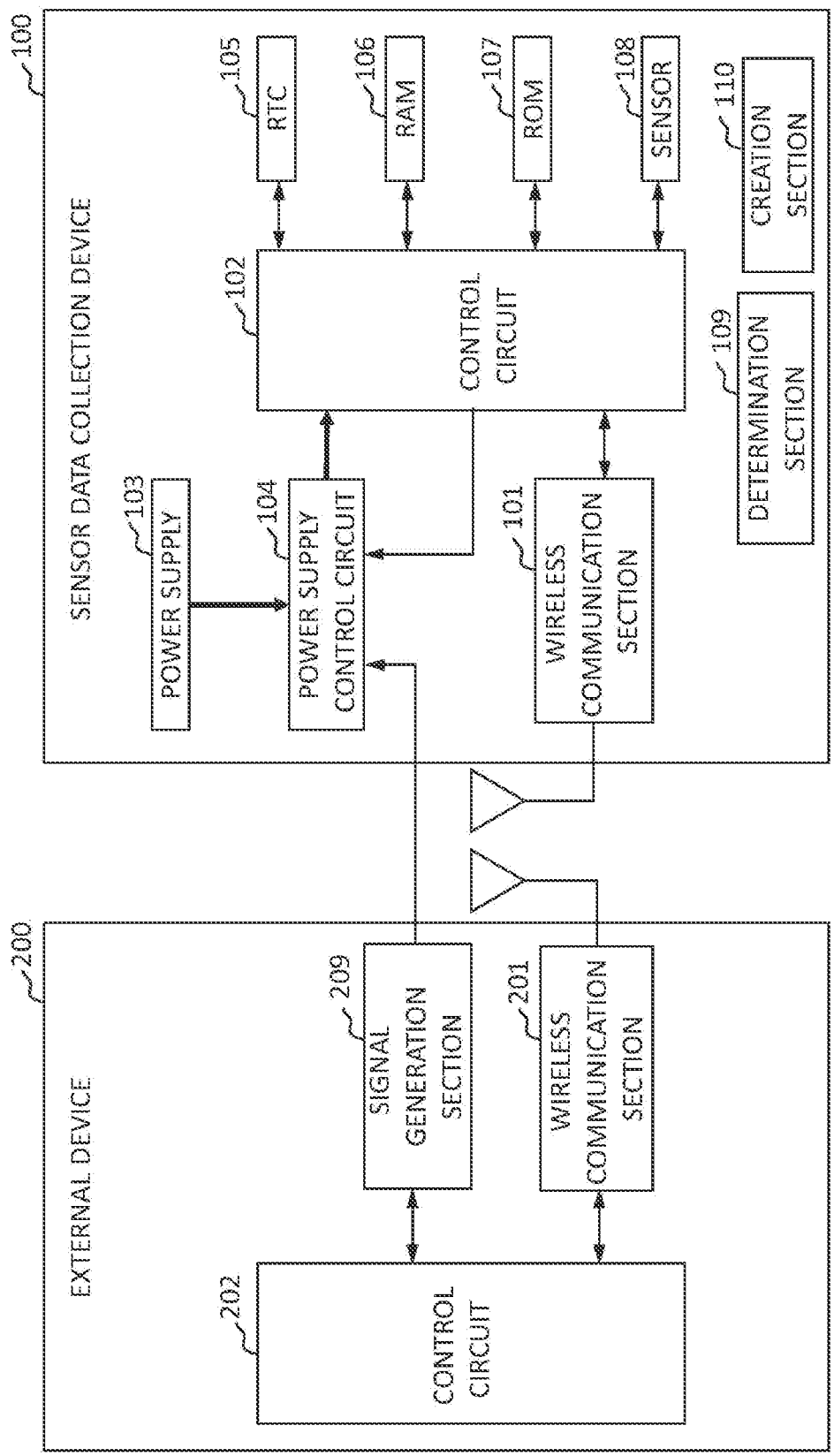
FIG. 7 is a diagram showing an example of a sensor data collection system according to a modified example of the embodiment.

FIG. 7 is a diagram showing an example of a sensor data collection system according to a modified example of the embodiment. A sensor data collection system 1a according to the modified example of the embodiment is provided with a sensor data collection device 100a and the external device 200. The sensor data collection system 1a is different from the sensor data collection system 1 described above in the point that the sensor data collection device 100a is provided instead of the sensor data collection device 100.

The sensor data collection device 100a is provided with the wireless communication section 101, a control circuit 102a, the power supply 103, the power supply control circuit 104, the real time clock 105, the RAM 106, the ROM 107, the sensor 108, a determination section 109, and a creation section 110.

Even when the power consumption during the power-off state is reduced using the configuration of the sensor data collection device 100 according to the embodiment described above, it can be assumed that the sufficient remaining battery level cannot be kept for completing the second operating state due to spontaneous discharge or the like of the battery.

Therefore, the sensor data collection device 100a measures the remaining battery level when the transition to the second operating state is made, and switches the processing in the second operating state when the remaining battery level is no higher than a predetermined threshold value. An example of the predetermined threshold value is set based on whether or not the remaining battery level of the power supply 103 is no lower than the electrical power necessary for transmitting the data accumulated in the ROM 107.

When the remaining battery level is insufficient, the sensor data collection device 100a transmits summary data of the data thus accumulated to the outside in advance. By adopting such a configuration, it is possible to ensure the provision of the minimum information necessary for the user.

Hereinafter, the configuration of the sensor data collection device 100a will specifically be described.

As the control circuit 102*a*, it is possible to apply the control circuit 102. It should be noted that the control circuit 102*a* makes the power supply control circuit 104 obtain information identifying the remaining battery level of the power supply 103 in the second operating state. The control circuit 102*a* obtains the information identifying the remaining battery level of the power supply 103 which the power supply control circuit 104 is made to obtain. The control circuit 102*a* obtains information identifying an amount of the data accumulated in the ROM 107.

The determination section 109 obtains the information identifying the remaining battery level of the power supply 103 and the information identifying the amount of the data accumulated in the ROM 107 from the control circuit 102*a*. The determination section 109 determines whether or not the remaining battery level of the power supply 103 is no lower than the electrical power necessary to transmit the data accumulated in the ROM 107 based on the information identifying the remaining battery level of the power supply 103 and the information identifying the amount of the data accumulated in the ROM 107 thus obtained.

The control circuit 102*a* obtains the determination result from the determination section 109. When the determination result thus obtained represents the fact that the remaining battery level of the power supply 103 is no lower than the electrical power necessary to transmit the data accumulated in the ROM 107, the control circuit 102*a* obtains the data accumulated in the ROM 107, and creates the sensor data notification which includes the data thus obtained, and the destination of which is the external device 200. The control circuit 102*a* outputs the sensor data notification thus created to the wireless communication section 101.

When the determination result thus obtained represents the fact that the remaining battery level of the power supply 103 is lower than the electrical power necessary to transmit the data accumulated in the ROM 107, the control circuit 102*a* obtains the data accumulated in the ROM 107, and then outputs the data thus obtained to the creation section 110.

The creation section 110 obtains the data output by the control circuit 102*a*, and then creates the summary data of the data thus obtained. An example of the summary data is what is obtained by extracting some of characteristic or representative values such as the number and a feature amount of the data accumulated in the ROM 107. Here, an example of the feature amount is a maximum value, a minimum value, an average value, a central value, a standard deviation, or the like. An example of the summary data can include one or some of the values obtained as a result of some operation performed on the data thus accumulated. Here, an example of the some operation is counting after performing binarization, a peak frequency after performing the FFT, or the like. It is desirable for the summary data to be light in weight.

The control circuit 102*a* obtains the summary created by the creation section 110 to create the sensor data notification which includes the summary thus obtained, and the destination of which is the external device 200. The control circuit 102*a* outputs the sensor data notification thus created to the wireless communication section 101.

In the embodiment described above, a part or the whole of the processing of the control circuit 102*a*, the determination section 109, and the creation section 110 can also be a functional section (hereinafter referred to as a software functional section) realized by a processor such as a CPU executing a program stored in the ROM 107. It should be noted that a part or the whole of the processing of the control circuit 102*a*, the determination section 109, and the creation section 110 can also be realized by hardware such as an LSI, an ASIC, or an FPGA, or can also be realized by a combination of the software functional section and the hardware.

(Operation of Sensor Data Collection System)

An operation of the sensor data collection system will be described.

Since FIG. 3 can be applied to the operation when the sensor data collection device 100 is in the first operating state in the sensor data collection system, the description thereof will be omitted here.

Figure 8:
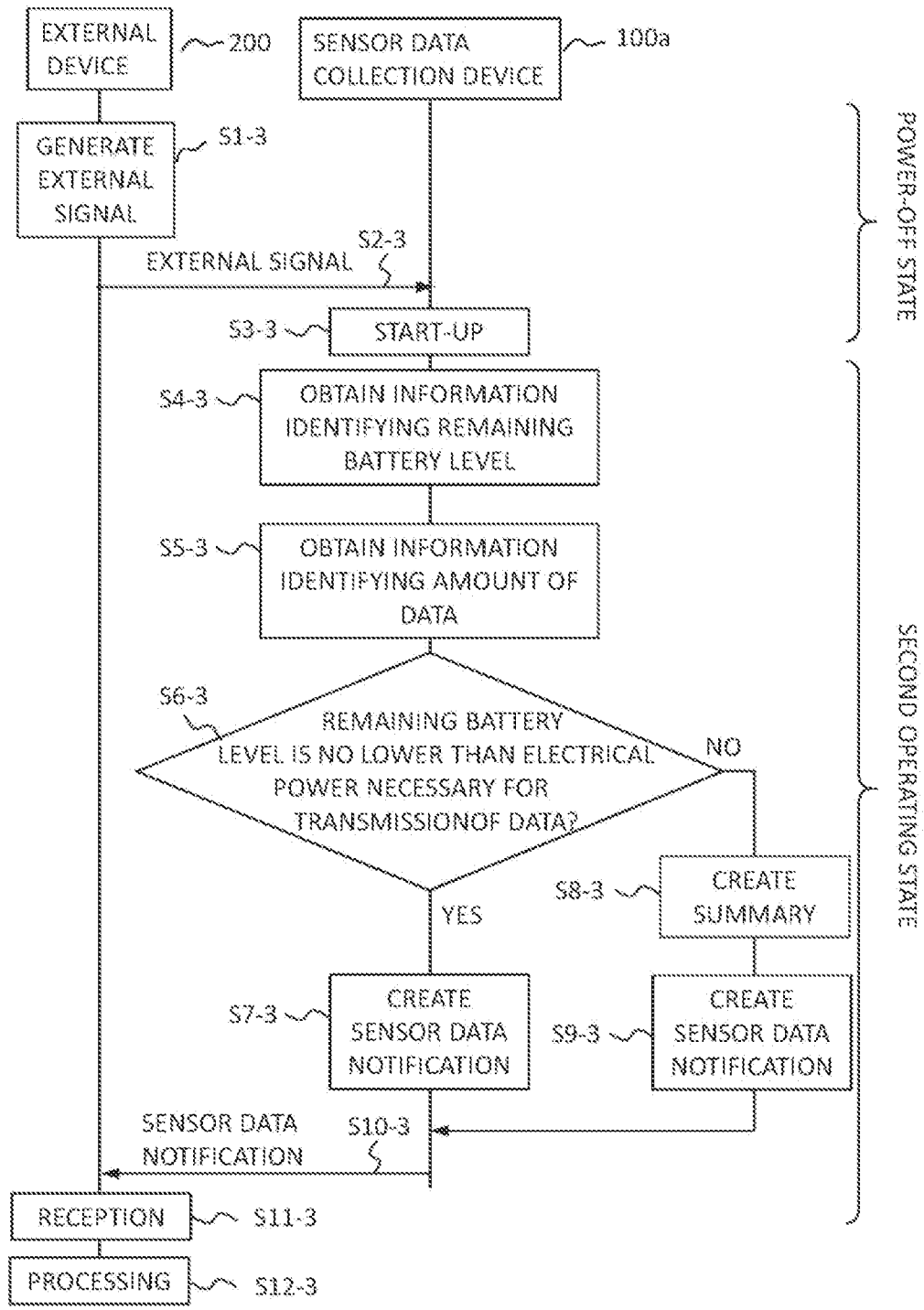
FIG. 8 is a flowchart showing an example of an operation of the sensor data collection system according to the modified example of the embodiment.

FIG. 8 is a flowchart showing an example of the operation of the sensor data collection system according to the modified example of the embodiment. The operation when the sensor data collection device 100*a* is in the power-off state and the second operating state in the sensor data collection system will be described with reference to FIG. 8.

Since the steps S1-2 through S3-2 described with reference to FIG. 5 can be applied to the steps S1-3 through S3-3, the description thereof will be omitted here.

(Step S4-3)

In the sensor data collection device 100*a*, the control circuit 102*a* makes the power supply control circuit 104 obtain the information identifying the remaining battery level of the power supply 103. The control circuit 102*a* obtains the information identifying the remaining battery level of the power supply 103 which the power supply control circuit 104 is made to obtain.

(Step S5-3)

In the sensor data collection device 100*a*, the control circuit 102*a* obtains the information identifying the amount of the data accumulated in the ROM 107.

(Step S6-3)

In the sensor data collection device 100*a*, the determination section 109 obtains the information identifying the remaining battery level of the power supply 103 and the information identifying the amount of the data accumulated in the ROM 107 from the control circuit 102*a*. The determination section 109 determines whether or not the remaining battery level of the power supply 103 is no lower than the electrical power necessary to transmit the data accumulated in the ROM 107 based on the information identifying the remaining battery level of the power supply 103 and the information identifying the amount of the data accumulated in the ROM 107 thus obtained.

(Step S7-3)

In the sensor data collection device 100*a*, when the determination result thus obtained represents the fact that the remaining battery level of the power supply 103 is no lower than the electrical power necessary to transmit the data accumulated in the ROM 107, the control circuit 102*a* obtains the data accumulated in the ROM 107, and creates the sensor data notification which includes the data thus obtained, and the destination of which is the external device 200.

(Step S8-3)

In the sensor data collection device 100*a*, the control circuit 102*a* obtains the determination result from the determination section 109. When the determination result thus obtained represents the fact that the remaining battery level of the power supply 103 is lower than the electrical power necessary to transmit the data accumulated in the ROM 107, the control circuit 102*a* obtains the data accumulated in the ROM 107, and then outputs the data thus obtained to the creation section 110. The creation section 110 obtains the data output by the control circuit 102*a*, and then creates the summary of the data thus obtained.

(Step S9-3)

In the sensor data collection device 100a, the control circuit 102a obtains the summary created by the creation section 110 to create the sensor data notification which includes the summary thus obtained, and the destination of which is the external device 200.

(Step S10-3)

In the sensor data collection device 100a, the control circuit 102a outputs the sensor data notification thus created to the wireless communication section 101. The wireless communication section 101 obtains the sensor data notification output by the control circuit 102a, and then transmits the sensor data notification thus obtained to the external device 200.

(Step S11-3)

In the external device 200, the wireless communication section 201 receives the sensor data notification transmitted by the sensor data collection device 100a.

(Step S12-3)

In the external device 200, the control circuit 202 obtains the sensor data notification received by the wireless communication section 201. The control circuit 202 performs the predetermined processing on the sensor data notification thus obtained.

In the flowchart shown in FIG. 8, the step S3-3 corresponds to the power-off state, and the steps S4-3 through S10-3 correspond to the second operating state.

According to the sensor data collection system 1a related to the modified example of the embodiment, the sensor data collection device 100a is further provided with the determination section 109 for determining whether or not the remaining battery level is sufficient to transmit the data accumulated in the ROM 107 and the creation section 110 for creating the summary of the data accumulated in the ROM 107 when the determination section 109 has determined that the remaining battery level is not sufficient to transmit the data in the second operating state in the sensor data collection device 100. The control circuit 102a makes the wireless communication section 101 transmit the summary of the data created by the creation section 110 to the outside in the case of the second operating state.

By adopting such a configuration, it is possible for the sensor data collection device 100a to transmit the summary of the data accumulated to the outside even when the remaining battery level is not sufficient to complete the second operating state in the beginning of the second operating state. Therefore, it is possible to ensure the provision of the minimum data necessary for the user.

Application Examples

Application examples of the sensor data collection system 1 according to the present embodiment and the sensor data collection system 1a according to the modified example of the embodiment will be described.

(Endoscopic Capsule)

The sensor data collection device 100 included in the sensor data collection system 1 and the sensor data collection device 100a included in the sensor data collection system 1a are applied to a sensing device encapsulated in an endoscopic capsule or the like.

The sensing device incorporates a sensor such as a camera, a temperature sensor, or a chemical sensor. It is possible for the sensing device to incorporate a plurality of sensors. The sensing device is completely sealed. By adopting such a configuration, it is possible to reduce an influence on a human body.

A patient ingests the sensing device through a mouth. The sensing device ingested by the patient performs the sensing of the biological information in the human body while passing through paths of digestive organs. The sensing device accumulates the biological information obtained by performing the sensing inside the sensing device.

The patient is made to take the endoscopic capsule by a doctor in a hospital. Subsequently, the patient lives a daily life until the endoscopic capsule is discharged from the human body. The endoscopic capsule discharged from the human body is preserved by the patient him- or herself. When meeting with the doctor next time, there are performed an observational study and an analysis of the data stored in the sensing device sealed in the endoscopic capsule discharged from the human body. The patient obtains the feedback regarding a medical treatment by the observational study and the analysis of the data.

The first operating state corresponds to a period from when the patient takes the endoscopic capsule to when the endoscopic capsule is discharged. The first operating state is a process in which a variety of sensors provided to the sensing device sealed in the endoscopic capsule operate, and at the same time, the data is accumulated.

The second operating state is a process in which the doctor receives the endoscopic capsule from the patient to retrieve the data accumulated in the sensing device sealed in the endoscopic capsule thus received.

By applying the sensor data collection device 100 and the sensor data collection device 100a to the sensing device encapsulated in the endoscopic capsule or the like, the sensing device encapsulated in the endoscopic capsule does not consume the electrical power at all in the standby period from when the endoscopic capsule is discharged from the human body to when the doctor receives the endoscopic capsule.

Those in which the sensing device consumes the electrical power in the standby period from when the endoscopic capsule is discharged from the human body to when the doctor receives the endoscopic capsule are required to be provided with a contact or contactless charging mechanism for compensating the electrical power lacking due to the consumption of the electrical power by the sensing device.

In comparison to the above, those in which the sensor data collection device 100 and the sensor data collection device 100a are applied to the sensing device are not required to be provided with the charging mechanism since the electrical power is not consumed by the sensing device in the standby period from when the endoscopic capsule is discharged from the human body to when the doctor receives the endoscopic capsule and the sensing device can thus be made small in size and simple. Since it is possible to make the sensing device small and simple, it is possible to make the endoscopic capsule small and simple.

Further, regarding those obtained by applying the sensor data collection device 100 and the sensor data collection device 100a to the sensing device, since the electrical power is not consumed by the sensing device, the patient is not required to meet the doctor to return the endoscopic capsule immediately after the endoscopic capsule is discharged. Since it is possible to continue to keep the endoscopic capsule for the convenience of the patient to some extent, it is possible to enhance the convenience.

(Telemetry)

The sensor data collection device 100 included in the sensor data collection system 1 and the sensor data collection device 100a included in the sensor data collection system 1a are applied to the telemetry.

The telemetry (remote information collection) means transmitting measurement data of the user located at a remote location to a control center to manage the measurement data in the control center. In the telemetry, the process is automatized, the data is transmitted to a specific point such as a control center, and the data thus transmitted is collected.

Here, as an example of the telemetry, there is described a case where the present disclosure is applied to bio-logging. The bio-logging means a recorder which is attached to an animal, and with which data can be collected by the animal itself instead of a human.

Either one of the sensor data collection device 100 and the sensor data collection device 100a is attached to a living thing such as a wild animal (a living thing). An example of the wild animal is a bird such as a penguin, a mammal such as a seal or a dolphin, or a fish such as a carp or a shark.

Due to the variety of sensors provided to either one of the sensor data collection device 100 and the sensor data collection device 100a attached to the wild animal, there are recorded the mode of life of the wild animal, environmental information of surroundings, and so on. It is ideal for the sensor attached to the wild animal to be retrieved after collecting the mode of life of the wild animal to which the sensor is attached, the environmental information of the surroundings, and so on for a certain period of time.

However, it is uncertain that either one of the sensor data collection device 100 and the sensor data collection device 100a attached to the wild animal can be retrieved within a supposed period. When the sensor data collection device attached to the wild animal is supposedly what consumes the electrical power during the standby period, there is a possibility that the implemented battery drains to thereby make it unachievable to retrieve the data accumulated. Further, when the contact or contactless charging mechanism for compensating the electrical power lacking due to the consumption of the electrical power is provided in order to prevent the data accumulated from becoming unretrievable due to the drain of the mounted battery, the sensor data collection device grows in size.

In comparison to the above, when either one of the sensor data collection device 100 and the sensor data collection device 100a is attached to the wild animal, since the electrical power is not consumed during the standby period from when the measurement is completed to when the sensor data collection device is retrieved, the charging mechanism and so on are unnecessary. Therefore, since it is possible to prevent the sensor data collection device from growing in size with a small device such as the charging mechanism, it is possible to track the wild animal without making the wild animal feel stress. It becomes possible to observe the natural mode of life of the living thing while minimizing the influence caused by attaching the sensor data collection device 100 and the sensor data collection device 100a.

Although the embodiment of the present disclosure is hereinabove described, the embodiment is illustrative only, and it is not intended to limit the scope of the present disclosure. The embodiment can be implemented in other various aspects, and a variety of omissions, replacements, and modifications can be made within the scope or the spirit of the present disclosure. The embodiment and the modified example thereof include, for example, what can easily be conceived by those skilled in the art, what is substantially the same, and what is within an equivalent range.

For example, it is also possible to arrange to record a computer program for realizing the functions of the respective devices described above on a computer-readable recording medium, and make a computer system retrieve the computer program recorded on the recording medium to execute the computer program. It should be noted that the "computer system" mentioned here can be what includes an OS and hardware such as a peripheral device.

Further, the "computer-readable recording medium" means a storage device such as a portable medium such as a flexible disk, a magneto-optical disk, a ROM, a writable nonvolatile memory such as a flash memory, or a DVD (Digital Versatile Disc), or a hard disk drive incorporated in the computer system.

Further, the "computer-readable recording medium" should include those holding a program for a certain period of time such as a volatile memory (e.g., a DRAM (Dynamic Random Access Memory)) in the computer system to be a server or a client when transmitting the computer program via a network such as the Internet, or a communication line such as a telephone line.

Further, the program described above can be transmitted from the computer system having the program stored in the storage device or the like to another computer system via a transmission medium or with a transmission wave in the transmission medium. Here, the "transmission medium" for transmitting the program means a medium having a function of transmitting information such as a network (a communication network) such as the Internet or a communication line (a communication wire) such as a telephone line.

Further, the program described above can be for realizing a part of the function described above.

Further, the program described above can be a program, which can realize the function described above in combination with a program having already been recorded on the computer system, namely a so-called differential file (a differential program).

What is claimed is:

1. A sensor data collection device comprising:
    a power supply;
    a power supply control circuit configured to control the power supply;
    a sensor configured to perform sensing to thereby obtain data;
    a memory configured to store the data obtained by the sensor; and
    a control circuit configured to control the power supply control circuit, the sensor, and the memory, wherein
    the power supply control circuit supplies the sensor, the memory, and the control circuit with electrical power supplied by the power supply,
    the control circuit makes a transition to any one of a plurality of operating states, and makes the power supply control circuit shut off the electrical power supplied by the power supply to transit to a power-off state after a first operating state is completed and before a transition to a second operating state is made, the first operating state and the second operating state being included in the plurality of operating states, the power-off state being a state in which the power supply and a circuit coupled to the power supply control circuit are electrically disconnected by the power supply control circuit, and
    the control circuit further includes:
        a determination section configured to determine whether or not there remains a battery level for transmitting data accumulated in the memory in the second operating state, and a creation section configured to create a summary of the data accumulated in the memory when the determination section determines that the battery level for transmitting the data does not remain, and the control circuit makes a wireless communication section transmit the summary of the data created by the creation section external to the sensor data collection device in the second operating state.

2. The sensor data collection device according to claim 1, wherein the power supply is a primary cell or a secondary cell.

3. The sensor data collection device according to claim 2, wherein the power supply control circuit includes a switch and a switch control circuit, and the switch control circuit opens the switch to thereby shut off the electrical power to be supplied by the power supply.

4. The sensor data collection device according to claim 3, wherein the power supply control circuit starts the first operating state or the second operating state based on an external signal.

5. The sensor data collection device according to claim 4, wherein the switch control circuit includes a power generation element, and the switch control circuit generates the external signal with electrical power generated by the power generation element.

6. The sensor data collection device according to claim 5, wherein the power generation element is a photovoltaic generation element, and the switch control circuit generates the external signal with photovoltaic power caused by light irradiation to the photovoltaic generation element.

7. The sensor data collection device according to claim 1, wherein the control circuit makes the sensor periodically obtain data, and then makes the memory store the data obtained in the first operating state, and makes a wireless communication section transmit data accumulated in the memory external to the sensor data collection device in the second operating state.

8. The sensor data collection device according to claim 1, wherein the control circuit makes the power supply control circuit shut off the electrical power to be supplied by the power supply when an exceptional matter occurs during an operation.

9. The sensor data collection device according to claim 1, wherein the control circuit transmits a power-off signal to the power supply control circuit when the control circuit makes the power supply control circuit shut off the electrical power to be supplied by the power supply, and the power-off signal is transmitted to the power supply control circuit via a signal holding circuit.

10. The sensor data collection device according to claim 9, wherein the signal holding circuit is configured including a capacitor and holds a charge.

11. A sensor data collection system comprising:

the sensor data collection device according to claim 1; and an external device which is configured to generate an external signal for making the sensor data collection device start the second operating state after the sensor data collection device makes the power supply control circuit shut off the power to be supplied by the power supply.

12. A sensor data collection device, comprising: a power supply;

a power supply control circuit configured to control the power supply;

a sensor configured to perform sensing to thereby obtain data;

a memory configured to store the data obtained by the sensor; and a control circuit configured to control the power supply control circuit, the sensor, and the memory, wherein the power supply control circuit supplies the sensor, the memory, and the control circuit with electrical power supplied by the power supply, the control circuit makes a transition to any one of a plurality of operating states, and makes the power supply control circuit shut off the electrical power supplied by the power supply after a first operating state is completed and before a transition to a second operating state is made, the first operating state and the second operating state being included in the plurality of operating states, and the control circuit further includes a determination section configured to determine whether or not there remains a battery level for transmitting data accumulated in the memory in the second operating state, and a creation section configured to create a summary of the data accumulated in the memory when the determination section determines that the battery level for transmitting the data does not remain, and the control circuit makes a wireless communication section transmit the summary of the data created by the creation section external to the sensor data collection device in the second operating state.

13. A method of collecting sensor data to be executed by a sensor data collection device including a power supply, a power supply control circuit configured to control the power supply, a sensor configured to perform sensing to thereby obtain data, a memory configured to store the data obtained by the sensor, and a control circuit configured to control the power supply control circuit, the sensor, and the memory, the method comprising:

supplying, by the power supply control circuit, the sensor, the memory, and the control circuit with electrical power supplied by the power supply; and making, by the control circuit, the power supply control circuit shut off the electrical power supplied by the power supply to transit to a power-off state after a first operating state is completed, and before a transition to a second operating state is made, wherein the power-off state is a state in which the power supply and a circuit coupled to the power supply control circuit are electrically disconnected by the power supply control circuit, wherein the control circuit further includes:

a determination section configured to determine whether or not there remains a battery level for transmitting data accumulated in the memory in the second operating state, and a creation section configured to create a summary of the data accumulated in the memory when the determination section determines that the battery level for transmitting the data does not remain, and the control circuit makes a wireless communication section transmit the summary of the data created by the creation section external to the sensor data collection device in the second operating state.

\* \* \* \* \*